US006719986B1

(12) United States Patent
Wohlrab et al.

(10) Patent No.: US 6,719,986 B1
(45) Date of Patent: Apr. 13, 2004

(54) HYALURONATE LYASE USED FOR PROMOTING PENETRATION IN TOPICAL AGENTS

(75) Inventors: Wolfgang Wohlrab, Halle (DE); Reinhard Neubert, Halle (DE); Christoph Huschka, Halle (DE); Peter-Jürgen Müller, Jena (DE); Jörg-Herman Ozegowski, Jena (DE); Dieter Koegst, Osterweddingen (DE); Gerhard Fries, Osterweddingen (DE)

(73) Assignee: esparma GmbH, Osterweddingen (DE)

( * ) Notice: Subject to any disclaimer, the term of this patent is extended or adjusted under 35 U.S.C. 154(b) by 0 days.

(21) Appl. No.: 09/869,087

(22) PCT Filed: Dec. 22, 1999

(86) PCT No.: PCT/EP99/10337

§ 371 (c)(1),
(2), (4) Date: Sep. 5, 2001

(87) PCT Pub. No.: WO00/38732

PCT Pub. Date: Jul. 6, 2000

(30) Foreign Application Priority Data

Dec. 23, 1998 (DE) .......................................... 198 60 545

(51) Int. Cl.[7] ................................................. A61K 6/00
(52) U.S. Cl. ........................ 424/401; 424/450; 424/489; 424/94.1; 424/94.5; 424/94.62; 514/937; 514/938; 514/944; 514/946; 514/947
(58) Field of Search ................................. 424/401, 450, 424/94.1, 94.5, 94.62, 489; 514/937, 938, 944, 946, 947

(56) References Cited

U.S. PATENT DOCUMENTS

| 4,303,676 A | 12/1981 | Balazs |
| 5,571,503 A | 11/1996 | Mausner |

FOREIGN PATENT DOCUMENTS

| BE | 856006 | * | 12/1977 |
| DE | 197 23 308 A1 | | 12/1998 |
| FR | 2 448 903 A | | 10/1980 |
| GB | 1060513 | | 3/1967 |
| GB | 1179787 | | 1/1970 |
| HU | 57038 | * | 11/1991 |
| JP | 60243633 | * | 5/1987 |
| JP | 62-104579 A | | 5/1987 |
| JP | 9-98739 A | | 4/1997 |
| JP | 11-124401 A | | 5/1999 |
| KR | 9400998 B1 | | 2/1994 |

OTHER PUBLICATIONS

Popovici. Modification of the cutaneous permebility following the application of dermal preparations. II. effect of hyaluronidase o the qactivity of ointment containing antibiotics. Farmacia. 1973. 21(8), 479–89.*
U.S. patent application Ser. No. 09/868,955, Wohlrab et al., filed Jun. 22, 2001.
International Search Report for PCT/EP99/10337 mailed Apr. 27, 2000.

(List continued on next page.)

Primary Examiner—Thurman K. Page
Assistant Examiner—Lakshmi Channavajjala
(74) Attorney, Agent, or Firm—Leydig, Voit & Mayer, Ltd.

(57) ABSTRACT

The invention relates to an agent for treating skin diseases and/or functional disorders of the skin on the basis of different medicaments and/or auxiliary substances through promotion of penetration from topical formulations into the skin. According to the invention, the agent is composed of a hyaluronate lyase produced by microbial means and a medicament, preferably a hydrophilic medicament and/or auxiliary substances in different galenic formulations including colloidal carrier systems. The areas of application for the invention in human and veterinary medicament relate to the treatment, prophylaxis and/or metaphylaxis of skin diseases, functional disorders of the skin, the processes of skin ageing and dry skin conditions.

18 Claims, 2 Drawing Sheets

OTHER PUBLICATIONS

Greiling et al. "On the Heterogeneity of Hyaluronate Lyase" *Z. Physiol Chem.*, vol. 340 (1965).

Galikeev, Kh. L. "The Role of Hyaluronidase of Streptococci in the Mechanism of Corpuscula Antigen Resorption and it's Penetration Throught the Mucous Barrier of Respiratory Tracts" *Z. Mikrobiol., Epidemiol., Immunobiol.*, 44 (3), 60–3 (1967).

Jedrzejas et al. "Expression and Purification of Streptococcus Pneumoniae Hyaluronate Lyase from *Escherichia Coli*" *Protein Expression and Purification*, 13 (1), 83–9 (Jun. 1998).

* cited by examiner

II. Penetration of urea from formulations containing hyaluronate lyase in comparison with standard emulsions
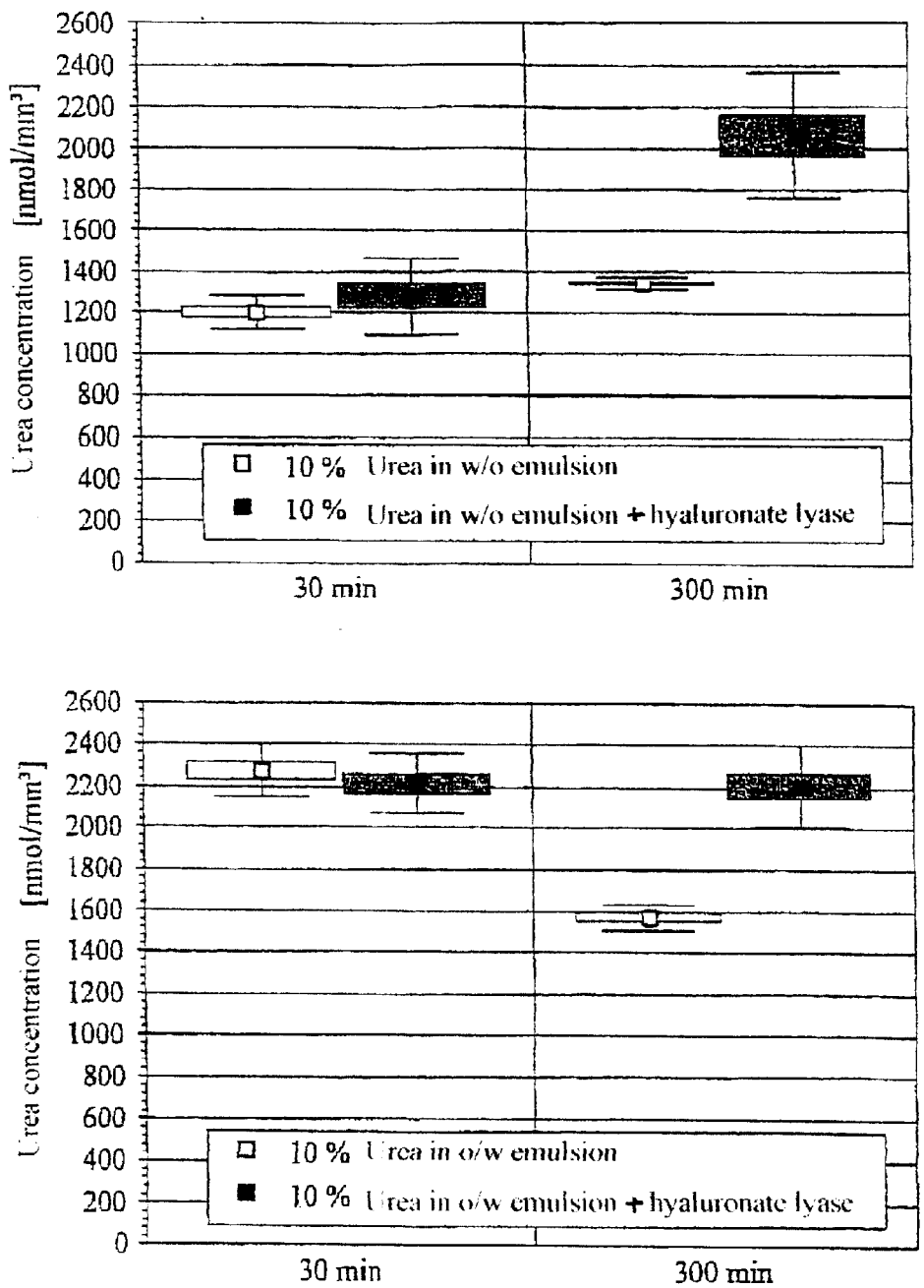
Figure 1  Penetration of urea from DAB emulsions into the stratum corneum of human skin ex vivo ($p \leq 0.05$, $n = 3$)

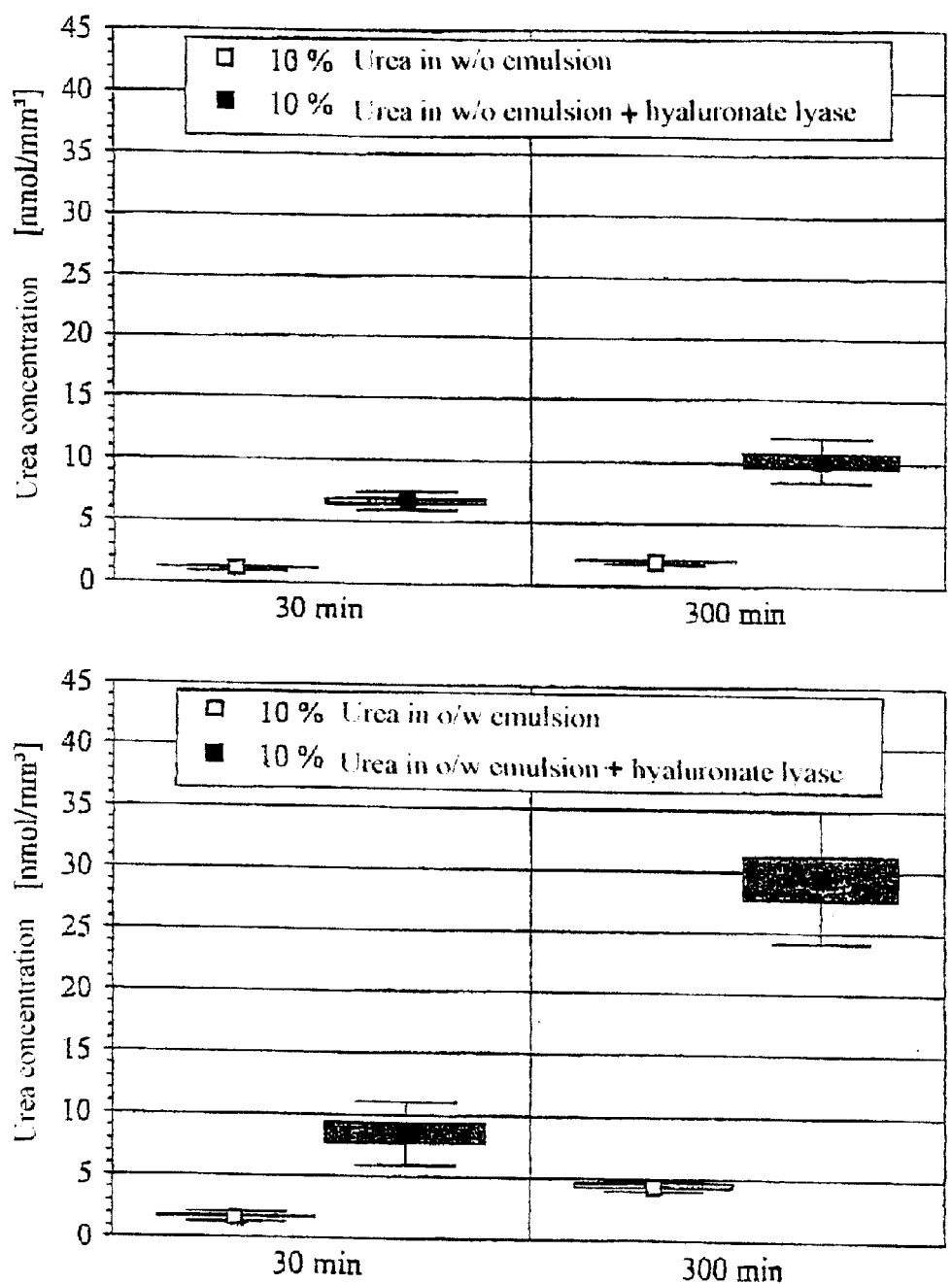
Figure 2 Penetration of urea from DAB emulsions into the epidermis of human skin ex vivo ($p \leq 0.05$, $n = 9$)

HYALURONATE LYASE USED FOR PROMOTING PENETRATION IN TOPICAL AGENTS

The invention relates to an agent which can be applied topically and which contains hyaluronate lyases for penetration modulation of one or more active substances and/or medicaments for cosmetic and medical treatment of skin, mucosa, hair and/or nails, such as e.g. for treatment of diseases or functional disorders of human or animal skin, mucosa, hair and/or nails.

Medicaments and/or active substances are used together with auxiliary substances in the form of liquid, semi-solid or even solid formulations of differing composition for the treatment, prophylaxis and metaphylaxis of functional and structural disorders of the skin and/or mucosa. In dependence on the physicochemical properties of the active substance or medicament, of the base used and of the auxiliary substances contained therein as well as of the nature of the area of the skin to be treated, the active substance molecules penetrate via different penetration mechanisms into the skin; in the given case they penetrate the latter until they are re-absorbed by the vascular system.

The skin is characterised by its natural function as a barrier in relation to its surroundings. Thus it can counteract the penetration of externally applied substances and/or substance mixtures. The active substances and/or medicaments used or respectively the co-applied auxiliary substances must overcome the barrier of the stratum corneum in order to spread the effect in the desired tissue layer (epidermis, dermis or even in the follicles and the vascular system).

It has already been known for a long time that through the presence of one or more special auxiliary substances the penetration of active substances can be made easier (penetration modulation). These substances are here in a position to alter, via different active mechanisms which are to some extent not completely clarified, the penetration or permeation of active substances and/or medicaments.

The following have what is termed an "enhancer effect": dimethyl sulphoxide, dimethyl acetamide, dimethyl formamide, derivatives of polyethylene glycol and propylene glycol, polyoxyethylene ester, alkanolamides, alkanolamines, alkylamines, N-alkylpyrrolidones, diethylene glycol monoethyl ether or fatty acid glycol esters (U.S. Pat. No. 5,912,009), 1-dodecylazacycloheptane-2-one, menthol (U.S. Pat. No. 4,933,184), plant oils (U.S. Pat. No. 5,229,130) isopropyl myristate (U.S. Pat. No. 5,618,555), eucalyptus oil (U.S. Pat. No. 4,440,777), fatty acid esters of lactic acid (U.S. Pat. Nos. 5,882,676 and 5,952,000) and lecithin (U.S. Pat. No. 4,783,450).

In U.S. Pat. No. 5,296,222 is described a percutaneous release system which contains lactam compounds (e.g. 1-substituted azacycloheptane-2-one) and propylene glycol. U.S. Pat. Nos. 3,989,816 and 4,316,893 also describe the application of lactam compounds.

In the Japanese disclosure Pat. Ser. No. 91-251534, are described plasters with increased penetration capability for piroxicam through the presence of polyoxyethylene alkyl ether or alkanolamides as penetration accelerators for the basic medicament triacetin (U.S. Pat. No. 58,834,010). Additional penetration accelerators are proposed in U.S. Pat. No. 4,755,535 (azacycloalkene), U.S. Pat. No. 4,699,77 (1-dodecylazacycloheptan-2-one and urea to absorb albuterol), U.S. Pat. No. 4,820,711 and U.S. Pat. No. 4,557,934 (medicaments dissolved in Azone or Azone derivatives).

The protective rights U.S. Pat. No. 5,914,322 and U.S. Pat. No. 5,962,433 describes agents which can be used topically and which have therapeutic application in pathological and traumatic symptoms of the skin, in which hyaluronic acid is used to facilitate transport of the active substance. The compositions named in U.S. Pat. Nos. 5,624,916 and 5,631,242 contain hyaluronic acid, urea and a pharmaceutical auxiliary and/or active substance with broad application for treating different skin and mucosa diseases.

To increase the penetration of hydrophilic substances, enzymes have also been proposed as penetration accelerators. The penetration-enhancing property of hyaluronidase of animal origin, especially obtained from bovine testes, is known. It is used for example in ointment form [Steinhaus, Christian and Sperandio, J. Amer. Pharmac. Assoc. Sci. Edit. 44,483 (1955) and Kalentey and Stenszky, Pharmazie 15,158, (1960)].

A transdermal release system having penetration accelerators is described in the French protective rights numbers 2,448,903 and 2,556,218. The transdermal agents contain in addition to the medicaments or active substances such as e.g. an antibiotic (tetracyline) and/or a local anaesthetic (lidocaine) and/or anti-inflammatory medicaments and/or an emulsifying or a mucolytic active substance, vitamin A and, as an auxiliary substance, sodium glycerol stereate and/or a plurality of enzymes as penetration-enhancing additives. Hyaluronidase, streptokinase, streptodornase, trypsin, chymotrypsin, alph-chymotrypsin, alpha-amylase, bromelain, papain, deoxyribonuclease, collagenase and subtilisin have been proposed as enzymes.

Disadvantageous about the known systems for enhancing penetration is that they can lead to irritations of the skin. The presence of proteases, and also of the solvents proposed as penetration accelerators, leads in some degree to direct damage of the skin. When hyaluronidases of bovine origin are used, there is the risk of transmitting infectious or antigenic material since generally speaking they still contain large amounts of other animal proteins (also other enzymes). The U.S. Pat. No. 4,152,212 proposes an intensive purifying process for a raw product of a hyaluronidase obtained from bovine testes or from liver tissue.

What is disadvantageous inter alia about the use of the bovine testes hyaluronidase and also of other hyaluronidases of animal origin is that the enzyme, as a result of the high foreign protein content, leads even after expensive purifying steps only to a product with low specific activity. Thus per $cm^2$ of skin only activities smaller than 1,000 IU can be applied. In the meantime preparations from bovine products to be applied in humans are hardly used any more on account of the high risk of transmitting bovine spongiform encephalopathy (BSE). What is furthermore disadvantageous is that the hyaluronidase is strongly inhibited by sulphated glycosaminoglycans which occur in the skin and generally in the extra-cellular matrix. Thus the activity of the enzyme in the skin when used as a penetration enhancer is substantially worsened.

Proceeding from this, the object of the present invention is to quote an agent for topical application, which makes possible an effective promotion of penetration of the active substances or medicaments contained in the agent. The agent should preferably be able to be used for therapeutic treatment and/or control of the function of the skin or mucosa.

This object preferably is achieved according to the invention. Advantageous embodiments and developments of the invention will be apparent from the description of the invention provided herein.

BRIEF DESCRIPTION OF DRAWINGS

FIG. 1 is a bar graph showing the penetration of urea from DAB emulsions into the stratum corneum of human skin ex vivo ($p \leq 0.05$, n=3).

FIG. 2 is a bar graph showing the penetration of urea from DAB emulsions into the epidermis of human skin ex vivo ($p \leq 0.05$, n=9).

According to the invention the penetration of medicaments is thus clearly improved if in addition to at least one or more active substances or medicaments, preferably hydrophilic active substances or medicaments, an enzyme of the type of a hyaluronate lyase (E.C. 4.2.2.1) is present as a penetration reinforcer in concentrations of 100 IU to 100,000 IU per g formulation, preferably in concentrations of 500 IU to 5,000 IU per g formulation, and the formulations are applied topically.

Generally one distinguishes three differently-acting types of enzymes which split hyaluronic acid (J. Ludowieg: The Mechanism of Hyaluronidases, JBC 236, 333–339, (1961)). First of all these are the endo-hydrolases which split the β-(1-3) bonds by hydrolysis. These include the majority of the hyaluronidases from higher organisms, for example hyaluronidase from bovine testes. These hyaluronate-glycan hydrolases (Enzyme class: E.C. 3.2.1.35/36) split, in addition to the bonds of hyaluronic acid, also other glycosaminoglycans to a limited extent. Endo-β-hyaluronidase from blood gel which splits the β-(1-4) bond in a highly specific manner, represents a further type. The third type of enzyme which is used according to the invention is hyaluronate lyase (Enzyme class: EC 4.2.2.1). This splits the hyaluronic acid in the β-(1-4) bonds according to an elimination mechanism forming a double bond in (4-5) position on the glucuronic acid. For lyases, endo- and exo-splitting mechanisms are quoted in the literature.

The hyaluronate lyase according to the invention is obtained by microbial fermentation. As the micro-organism is used in one embodiment, without thereby restricting the scope of protection, a microorganism of the type streptococcus, preferably a streptococcus of the serologic group B or C, in particular of the type *streptococcus agalactiae*.

Without restricting the invention in relation to the origin of the enzyme to a single microorganism, the invention will now be described by way of example with the aid of the enzyme obtained from *streptococcus agalactiae*. The enzyme produced from the culture liquids of this microorganism has an isoelectric point of IP=8.6 and a relative molar mass in the region of 116 kD and acts according to an endo-splitting mechanism. In the course of purifying and concentrating the enzyme from the culture filtrate of the submerged fermentation, in a further embodiment an enzyme dry agent is produced and introduced into the formulation as a dry agent with an activity of approximately 10,000 to 400,000 IU/mg dry weight.

In another embodiment, the hyaluronate lyase is introduced into the formulation as an aqueous buffered solution, possibly under the addition of stabilisers having concentrations between 10,000 IU/ml and 2,000,000 IU/ml.

The galenic formulation can be present in the form of a paste, ointment, cream, emulsion, gel or stick, preferably as an o/w emulsion. In the formulations, pharmaceutical carriers and/or hydrophilic and/or lipophilic active substances and/or auxiliary substances can be present. The hyaluronate lyase and/or the active substances and/or auxiliary substances can be present incorporated in colloidal carrier systems, preferably nanoparticles, liposomes or microemulsions. As the hydrophilic active substance, in addition to all the other hydrophilic medicaments for example 8-methoxypsoralen, urea, erythromycin, ciclopiroxolamine, all in the concentration range between 0.01 and 0.1 g per g formulation, or, in addition to all the other lipophilic medicaments, the lipophilic active substances minocyclin in the concentration range between 0.001 and 0.1 g per g formulation or glyceryl trinitrate in the concentration range between 0.01 and 0.5 g per g formulation can be present.

Advantageous about the formulations according to the patent is that when they are applied, no irritations of the skin occur which can be traced back to the enzyme hyaluronate lyase, even after several hours of exposure to the formulations. Through the high specific activity of the hyaluronate lyase or respectively its high purity it is possible to use very high activities per $cm^2$ skin surface.

The invention is now described below with the aid of 10 examples and penetration tests.

I. EXAMPLES

Source for the Base

1. Aqueous hydrophilic ointment as per DAB 10 with urea (DAB)

| | |
|---|---|
| Urea | 10.00% |
| Hyaluronate lyase (2500 IU/$cm^2$) | 1.30% |
| Lanette ® N (emulsifying cetyl stearyl alcobol DAB 10) | 9.00% |
| *Paraffinum subliquidum* (viscous paraffin) | 10.50% |
| *Vaselinum album* (white Vaseline) | 10.50% |
| *Aqua bidestillata* | ad 100.00% |

2. Aqueous wool alcohol ointment as per DAB with urea (DAB)

| | |
|---|---|
| Urea | 10.00% |
| Hyaluronate lyase (2500 IU/$cm^2$) | 1.30% |
| *Alcoholes Lanae* (wool alcohols) | 3.00% |
| Alcohol cetystearylicus (cetyl stearyl alcohol) | 0.25% |
| *Vaselinum album* (white Vaseline) | 46.75% |
| *Aqua bidestillata* | ad 100.00% |

3. Base cream DAC with polidocanol (free formulation)

| | |
|---|---|
| Polidocanol 600 | 5.00% |
| Hyaluronate lyase (2500 IU/$cm^2$) | 1.30% |
| Propylene glycol | 3.00% |
| *Aqua bidestillata* | 22.00% |
| Base cream DAC | ad 100.00% |

4. Hydrophilic triamcinolone acetonide cream (NRF)

| | |
|---|---|
| Triamcinolone acelonide (microfine) | 0.10% |
| Hyaluronate lyase (2500 IU/$cm^2$) | 1.30% |
| Medium chain triglycerides | 0.10% |
| Base cream DAC | ad 100.00% |

5. Hydrophilic hydrocortisone acetate cream (NRF)

| | |
|---|---|
| Hydrocortisone acetate | 1.00% |
| Hyaluronate lyase (2500 IU/$cm^2$) | 1.30% |
| Nonionic hydrophilic cream DAB | ad 100.00% |

6. Urea sodium chloride ointment (NRF)

| | |
|---|---|
| Urea | 10.00% |
| Sodium chloride | 10.00% |
| Hyaluronate lyase (2500 IU/$cm^2$) | 1.30% |
| Purified water | 30.00% |
| Wool alcohol ointment DAB | ad 100.00% |

7. Hydrophilic urea emulsion (NRF)

| | |
|---|---|
| Urea | 10.00% |
| Lactic acid (90%) | 1.00% |
| Hyaluronate lyase (2500 IU/$cm^2$) | 1.30% |
| Sodium lactate solution | 4.00% |
| Emulsion base NRF | ad 100.00% |

8. Urea cream with Tretinoin (free formulation)

| | |
|---|---|
| Urea | 12.00% |
| Tretinoin | 0.03% |
| Hyaluronate lyase (2500 IU/$cm^2$) | 1.30% |
| Base cream DAC | ad 100.00% |

-continued

| 9. Hydrophilic metronidazol gel (NRF) | |
|---|---:|
| Metronidazol | 0.75% |
| Propylene glycol | 5.00% |
| Sodium edetate | 0.10% |
| Trometamol | 0.25% |
| Polyacrylic acid | 0.50% |
| Potassium sorbate | 0.10% |
| Hyaluronate lyase (2500 IU/cm$^2$) | 1.30% |
| Purified water | ad 100.00% |
| 10. Unguentum Oxytetracyclini 1% L/W (SR) | |
| *Oxytetracyclinum hydrochloricum* | 1.00% |
| *Natrium aceticum* | 0.36% |
| *Mucilago hydroxyethylcellulosi* 8% ASR | 10.00% |
| *Unguentum emulsificans aquosum* NSR | 50.00% |
| Hyaluronate lyase (2500 IU/cm$^2$) | 1.30% |
| *Aqua conservata* ASR | ad 100.00% |

Translator's Footnotes

1. On page 5, line 32 of the German text, the word "Schleimheit" has been thought to be a typographical error for "Schleimhaut" and translated as the latter.
2. In the "Abstract", the word "Problemarzneistoff" has been rendered as "hazardous medicament" but there may be some technical term for this which I have been unable to trace.

What is claimed is:

1. A composition for topical application on human or animal skin and/or mucosa, comprising at least one active substance and hyaluronate lyase in concentrations of 100 IU to 100000 IU per g formulation as a penetration enhancer, wherein the hyaluronate lyase is obtained from a micro-organism by microbial fermentation and wherein the hyaluronate lyase belongs to EC 4.2.2.1.

2. The composition according to claim 1, wherein the hyaluronate lyase has been obtained from a micro-organism of the type streptococcus through microbial fermentation.

3. The composition according to claim 1, wherein the hyaluronate lyase has been obtained from a streptococcus of the type *streptococcus agalactiae* through microbial fermentation.

4. The composition according to claim 1, wherein the hyaluronate lyase has an isoelectric point in the region of IP=8.6, a relative molar mass in the region of 116 kD.

5. The composition according to claim 1, wherein the hyaluronate lyase concentration is in the range between 100 IU and 5000 IU.

6. The composition according to claim 1, wherein the hyaluronate lyase has been introduced in the composition in the form of a dry product which has an activity of roughly 10000 to 400000 IU/mg and is produced with the addition of one or more stabilizers though dehydration, especially through lyophilisation.

7. The composition according to claim 1, wherein the hyaluronate lyase has been introduced into the composition in the form of an aqueous buffered solution, with the addition of stabilizers, having concentrations of 10000 to 20000 IU/mg in this form.

8. The composition according to claim 1, wherein the composition is in the form of a paste, ointment, cream, emulsion, gel, or stick.

9. The composition according to claim 1, further comprising pharmaceutical carriers and/or hydrophilic and/or lipophilic active substances.

10. The composition according to claim 9, wherein the hyaluronate lyase and/or the active substances and/or the auxiliary substances are incorporated into a colloidal carrier system.

11. The composition according to claim 1, further comprising urea as a hydrophilic active substance in the concentration range between 0.01 and 0.4 g urea per g.

12. The composition according to claim 1, further comprising 8-methoxypsoralen as a lipophilic active substance in the concentration range between 0.001 and 0.1 g 8-methoxypsoralen per g composition.

13. The composition according to claim 1, further comprising erythromycin as a hydrophilic active substance in the concentration range between 0.001 and 0.1 g erythromycin per g composition.

14. The composition according to claim 1, further comprising minocyclin as a lipophilic active substance in the concentration range between 0.001 and 0.1 g minocyclin per g composition.

15. The composition according to claim 1, further comprising ciclopiroxolamine as a hydrophilic active substance in the concentration range between 0.001 and 0.1 g ciclopiroxolamine per g composition.

16. The composition according to claim 1, further comprising glyceryl trinitrate as a lipophilic active substance in the concentration range between 0.01 and 0.5 g glyceryl trinitrate per g composition.

17. The composition according to claim 1, wherein the composition is in the form of an o/w emulsion.

18. The composition according to claim 10, wherein the colloidal carrier system is selected from nanoparticles, liposomes, or microemulsions.

* * * * *